United States Patent

Wallschlaeger

[11] Patent Number: 5,345,381
[45] Date of Patent: Sep. 6, 1994

[54] SPIRAL SCAN COMPUTER TOMOGRAPHY APPARATUS

[75] Inventor: Heinrich Wallschlaeger, Erlangen, Fed. Rep. of Germany

[73] Assignee: Siemens Aktiengesellschaft, Munich, Fed. Rep. of Germany

[21] Appl. No.: 964,381

[22] Filed: Oct. 21, 1992

[30] Foreign Application Priority Data

Nov. 11, 1991 [DE] Fed. Rep. of Germany ....... 4137031

[51] Int. Cl.$^5$ ............................................. G06F 15/42
[52] U.S. Cl. ........................... 364/413.14; 364/413.13; 364/413.18; 364/723
[58] Field of Search ...................... 364/413.13, 413.14, 364/413.18, 723

[56] References Cited

U.S. PATENT DOCUMENTS 4,630,202 12/1986 Mori ................................. 364/413.15
4,789,929 12/1988 Nishimura ....................... 364/413.15

FOREIGN PATENT DOCUMENTS 0405862 1/1991 European Pat. Off. .
0450152 10/1991 European Pat. Off. .
0464645 1/1992 European Pat. Off. .
0483729 5/1992 European Pat. Off. .

Primary Examiner—Robert A. Weinhardt
Assistant Examiner—Gita Shingala
Attorney, Agent, or Firm—Hill, Steadman & Simpson

[57] ABSTRACT

A computer tomography apparatus undertakes a three-dimensional scanning of the examination subject with relative motion between the rotating measurement unit and the patient, the relative motion ensuing in the longitudinal direction of the patient support during the acquisition and processing of the detector data, so that a spiral scan is accomplished. For image reconstruction, data corresponding to the scanning of parallel slices are generated from the detector data by spiral interpolation, the interpolation being done with the detector data in the form of the relative intensities registered at the detector.

4 Claims, 2 Drawing Sheets

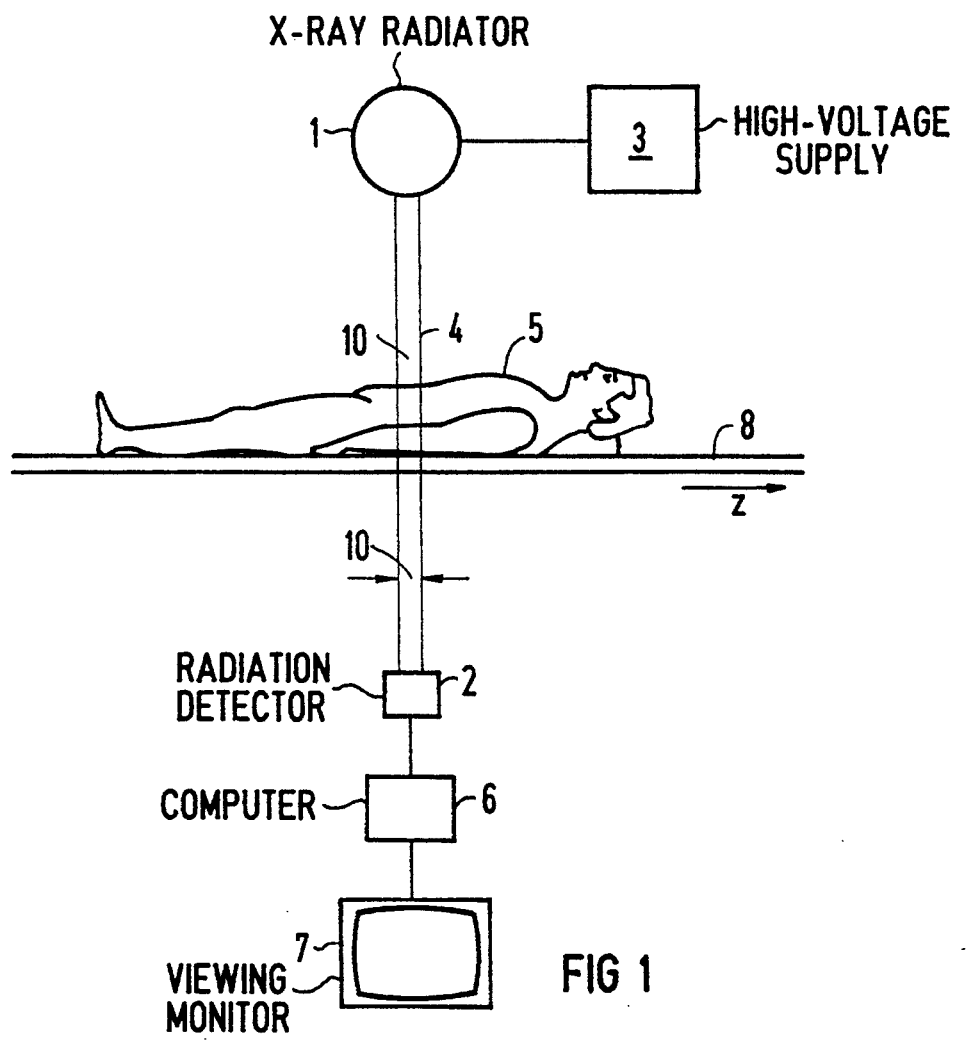
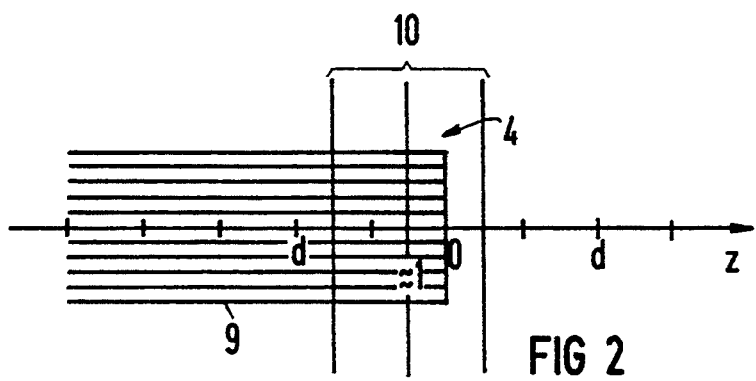

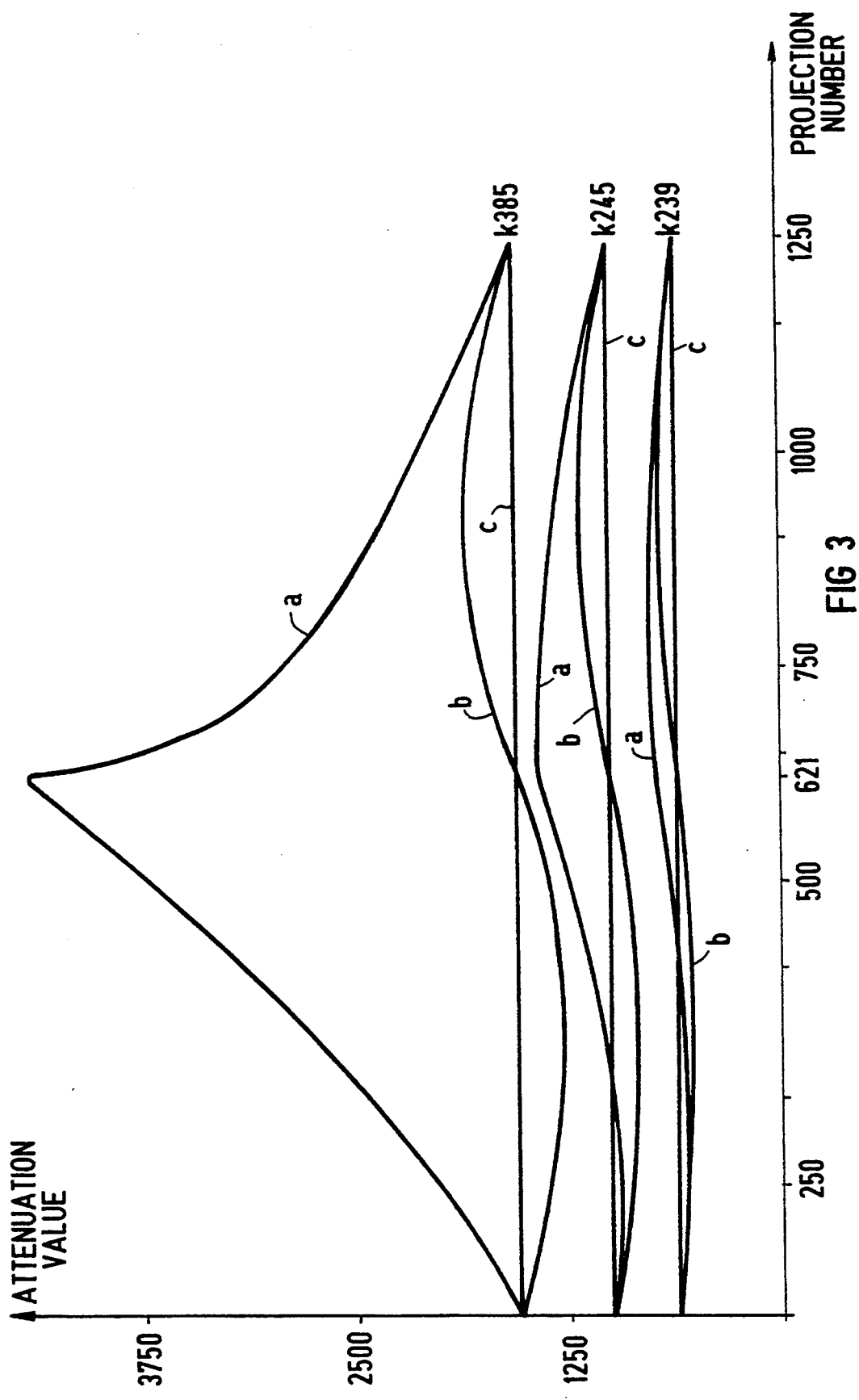

SPIRAL SCAN COMPUTER TOMOGRAPHY APPARATUS

BACKGROUND OF THE INVENTION

1. Field of the Invention

The present invention is directed to a computer tomography apparatus of the type wherein a spiral scan of an examination subject is undertaken.

2. Description of the Prior Art

Computer tomography systems are known wherein an examination subject is three-dimensionally scanned on the basis of relative motion between the measurement unit, consisting of an x-ray radiator and a radiation detector, and the patient support, with the patient thereon. The relative motion ensues in the longitudinal direction of the patient support during the acquisition and processing of the detector data, with the measurement unit rotating around the examination subject.

A scan of this type is known as a spiral scan. When registering the data for such spiral scans, the measured data arise at different z-positions (spiral data). The z-coordinate characterizes the relative position of the measured slice vis-a-vis the examination subject. The z-direction is thus oriented perpendicularly to the measured slice. The conventional tomographic reconstruction algorithm, however, employs data obtained for a constant z-position. For systems employing a spiral scan, therefore, interpolation algorithms have been developed which generate new data, by interpolation, corresponding to a planar slice from the spiral data before the actual image reconstruction. The goal of the interpolation is that the interpolated data are as close as possible to those which would actually be measured in a planar slice. Interpolation algorithms hitherto employed have always operated on the data in the form of attenuation values. Attenuation values are scaled line integrals or scaled logarithms of the relative intensities.

If a partial volume effect (i.e. a few objects of interest (organs) only partially project into the measured slice) is present, however, a problem arises in this known type of interpolation. In comparison to a true planar scan, the levels of the CT values of the affected objects and their contours are modified, and images which should actually be rotationally-symmetrical no longer appear symmetrical.

SUMMARY OF THE INVENTION

It is an object of the present invention to provide a spiral scan computer tomography apparatus with improved image quality in comparison to conventional systems of this type.

The above object is achieved in accordance with the principles of the present invention in a spiral scan computer tomography apparatus wherein data corresponding to the scan of parallel, planar slices are generated from the detector data by interpolation for image reconstruction, with the interpolation being undertaken employing detector data in the form of relative intensities. A theoretical analysis of the aforementioned circumstance of a partial volume effect shows that interpolation using data in the form of the relative intensities notably reduces the image distortion which would otherwise arise. In the case of an interpolation with data from the interval of $\pm\frac{1}{2}$ slice thickness around a reference position, the aforementioned image errors are completely eliminated.

In contrast to interpolation methods employed with spiral scans known in the art, wherein the interpolation weightings were applied to the attenuation values, instead the interpolation weightings are applied directly to the measured intensities in accordance with the principles of the present invention, i.e., in conventional interpolation techniques employing the attenuation values, it is necessary to work with logarithmized data, whereas in the apparatus and interpolation techniques disclosed herein, non-logarithmized data shall be used for the spiral interpolation.

DESCRIPTION OF THE DRAWINGS

FIG. 1 is schematic diagram showing the components of a spiral scan computer tomography apparatus, constructed in accordance with the principles of the present invention, necessary for explaining the invention.

FIG. 2 is an illustration of a measured slice obtained in a computer tomograph apparatus according to FIG. 1, for explaining the invention.

FIG. 3 shows a set of curves obtained using interpolation with attenuation values according to the prior art and interpolation using intensities according to the invention, compared with curves for an ideal value.

DESCRIPTION OF THE PREFERRED EMBODIMENTS

The relevant components of a spiral scan computer tomography apparatus, for explaining the principles of the present invention, are schematically shown in FIG. 1. The spiral scan computer tomography apparatus has a measurement unit consisting of an x-ray radiator 1 and a radiation detector 2, the measurement unit being rotatable around an examination subject 5. The x-ray radiator 1 is supplied by a high-voltage generator 3, and generates a planar x-ray beam 4 passing through the examination subject 5. The plane of the x-ray beam 4 extends perpendicularly to the plane of the drawing. The x-ray beam 4, attenuated by the examination subject 5, is incident on the radiation detector 2, which consists of a row of detector elements. Each detector element generates an output signal, the output signals being collectively supplied to a computer 6. The computer 6 calculates a quantity of planar images of the scanned volume of the examination subject 5 from these output signals, respectively for different z-positions. These images are reproduced on a viewing monitor 7.

For three-dimensional scanning of the examination subject 5, the measurement unit consisting of the x-ray radiator 1 and the radiation detector 2 is rotated around the examination subject 5, while the examination subject 5 is simultaneously shifted in the z-direction on a patient support 8. The examination subject 5 is thus spirally scanned by the x-ray beam 4.

In order to analyze the difference between the aforementioned known image calculation and image calculation corresponding to the invention, a central cylinder 9, shown in FIG. 2, shall be considered. The end face of the central cylinder 9 is assumed to be planar, and defines the reference plane at $z=0$. It is assumed for the relative motion between the measured slice 10 and the cylinder 9 that the feed during a 360° revolution of the measurement unit exactly corresponds to the thickness of the measured slice 10.

First, the intensities registered at the radiation detector 2 are identified taking the partial volume effect into consideration. When the cylinder 9 fully enters into the slice, the intensity $$I_{k,l}(z_1) = I_0 \exp(-\mu r_{k,l}) \text{ for } z_1 \leq -d/2 \quad (1)$$

is measured. The variable $z_1$ designates the middle of the measured slice 10, which moves in the +z-direction during the spiral scan. The slice 10 has a thickness d. The value $r_{k,l}$ is the path length of the beam of the $k^{th}$ channel of the $l^{th}$ projection within the cylinder 9, and $\mu$ is the x-ray absorption coefficient of the cylinder 9.

When the cylinder 9 only partially projects into the measured slice 10, the intensity is composed of the fraction $(d/2-z_1)/d$ of attenuated radiation and the fraction $(d/2+z_1)/d$ of unattenuated radiation. This results in results in an expression for the intensity of:

$$I_{k,l}(z_1) = I_0 \left[ \left( \frac{1}{2} - \frac{z_1}{d} \right) \exp(-\mu r_{k,l}) + \frac{1}{2} + \frac{z_1}{d} \right] \quad (2)$$

$$\text{for } -\frac{d}{2} \leq z_1 \leq \frac{d}{2}.$$

When the cylinder 9 no longer projects into the measured slice 10 at all, the radiation detector 2 receives the full signal:

$$I_{k,l}(z_1) = I_0 \text{ for } d/2 \leq z_1. \quad (3)$$

The relationship between intensities and attenuation values is established by $$S_{k,l} = f \cdot \ln \frac{I_0}{I_{k,l}} \quad (4)$$

wherein f is a multiplication factor.

The best result that a spiral algorithm can deliver is to provide data which are as close as possible to data which would be obtained in a planar scan in the reference plane. In the present instance, such data would be the attenuation values $$s_{k,l} = -f \cdot \ln \left[ \tfrac{1}{2}(1 + \exp(-\mu r_{k,l})) \right], \quad (5)$$

identical for all l.

As a result of the partial volume effect, which also arises in the planar scan, the attenuation value of a cylinder 9 half-projecting into the measured slice 10, however, is not established simply by $$s_{k,l} = f \tfrac{1}{2} \mu r_{k,l} \quad (6)$$

but instead is established by equation (5). As a result, the level in the image of the cylinder 9 is not constant, but varies. This occurs because the contribution to the total level made by the empty (air-filled) half of the measured slice 10 leads to a computational lowering of the attenuation in the inner region of the cylinder 9, as can be seen by comparing equations (5) and (6) for an extremely large $\mu r$.

A detailed example of the interpolation technique of the invention shall be set forth below using a specified interpolation rule. The inventive techniques, however, can be employed with other interpolation rules, as are known to those skilled in the art. For the interpolation employed in this example, data from the region of two successively measured slices are employed. If $z_1$ is the middle of the first slice, $z_1 + d$ is the middle of the second slice. Using this convention, the interpolation rule employed is as follows:

$$\hat{P}(0) = \left( 1 + \frac{z_1}{d} \right) P(z_1) - \frac{z_1}{d} P(z_1 + d). \quad (7)$$

Using this interpolation rule, P can be either intensity or attenuation. The index k can be omitted if a fixed (single) channel is considered, for example, that of the central ray. The index l is omitted, because it is unambiguously identifiable by the z-position.

The application of the interpolation weighting in accordance with the principles of the present invention is derived using equations (1 through 3) as follows:

$$\hat{I}(0) = \left( 1 + \frac{z_1}{d} \right) I(z_1) - \frac{z_1}{d} I(z_1 + d) \quad (8)$$

$$= \begin{cases} \left[ 1 + \frac{z_1}{d} \left( \frac{z_1}{d} + \frac{3}{2} \right) \right] I_0 \exp(-\mu r) - \frac{z_1}{d} \left( \frac{z_1}{d} + \frac{3}{2} \right) I_0 \text{ for } -d \leq z_1 \leq -\frac{d}{2} \\ \left( 1 + \frac{z_1}{d} \right) \left( \frac{1}{2} - \frac{z_1}{d} \right) I_0 \exp(-\mu r) + \left[ \left( 1 + \frac{z_1}{d} \right) \left( \frac{1}{2} + \frac{z_1}{d} \right) - \frac{z_1}{d} \right] I_0 \text{ for } -\frac{d}{2} \leq z_1 \leq 0. \end{cases}$$

The function curve for equation (8) has a shape as indicated by curves b in FIG. 3.

The application of the interpolation weighting to attenuation values yields:

$$\hat{S}(0) = \left( 1 + \frac{z_1}{d} \right) S(z_1) - \frac{z_1}{d} S(z_1 + d) \quad (9)$$

$$= \begin{cases} f \left( \left( 1 + \frac{z_1}{d} \right) \mu r + \frac{z_1}{d} \ln \left[ - \left( \frac{z_1}{d} + \frac{1}{2} \right) \exp(-\mu r) + \frac{z_1}{d} + \frac{3}{2} \right] \right) \text{ for } -d \leq z_1 \leq -\frac{d}{2} \\ - \left( 1 + \frac{z_1}{d} \right) f \cdot \ln \left[ \left( \frac{1}{2} - \frac{z_1}{d} \right) \exp(-\mu r) + \frac{1}{2} + \frac{z_1}{d} \right] \text{ for } -\frac{d}{2} \leq z_1 \leq 0. \end{cases}$$

The function curves for equation (9) are shown as curves a in FIG. 3.

In FIG. 3, the projection number is entered increasing toward the right and the attenuation value is entered increasing toward the top. As noted above, the curves a are based on an interpolation with attenuation values and the curves b are based on an interpolation with intensities. The curves c are derived from the ideal value. The curves are shown for different values of k. The curves shown for k=385 show the attenuation values for the beam through the center of the cylinder 9 (high attenuation). The curves illustrated for k=239 show the attenuation values for a beam which barely tangentially intersects the cylinder 9 (low attenuation).

Particularly for higher values of $\mu r$, the interpolation with attenuation values clearly leads to level shifts and to inhomogeneities. In comparison thereto, interpolation using intensities comes relatively close to the constant value according to equation (5)

$$\hat{S}(0) = -f \cdot \ln \tfrac{1}{2}[1 + \exp(-\mu r)] \quad z_1 \epsilon [-d, 0], \tag{10}$$

which would be measured in a planar scan in the reference plane, and which is indicated in FIG. 3 by a horizontal straight line. A noticeable improve can be seen in FIG. 3 using the interpolation technique employing intensities in accordance with the principles of the present invention.

Interpolation using intensities thus supplies demonstrably better results than interpolation using attenuation values. This is also true given employment of the inventive technique using other interpolation rules. The extent of the deviation of the interpolation using intensities from the ideal value according to equation (5) is dependent on the extent to which data are employed from those regions wherein the cylinder lies either entirely within, or entirely outside, the measured slice.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computer tomography apparatus comprising:
   means for conducting a spiral scan of an examination subject by directing radiation having an incident intensity at said subject and obtaining relative intensity signals representing relative intensity values for radiation passing through said subject;
   means for generating data representing an image of said examination subject, said image conforming to parallel slices of said examination subject, by spiral interpolation of said relative intensity values performed directly on said relative intensity signals; and
   means for constructing said image of said examination subject from said data.

2. A computer tomography apparatus as claimed in claim 1 wherein said means for generating data comprises means for spirally interpolating said relative intensity signals for a plurality of said parallel slices, each slice having a center and said centers having a center spacing therebetween, to obtain interpolated values by multiplying an intensity value obtained for a first parallel slice by the sum of one plus the quotient of the center for said first parallel slice divided by said center spacing, and subtracting therefrom the intensity value obtained for a second parallel slice at a center spacing from said first parallel slice multiplied by the quotient of said center for said first parallel slice and said center spacing, and wherein said means for reconstructing said image comprises means for reconstructing said image with attenuation values formed by a multiplication factor multiplied by the natural logarithm of the quotient of said interpolated values divided by said incident intensity.

3. A method for obtaining a computer tomogram of an examination subject comprising the steps of:
   conducting a spiral scan of an examination subject by directing radiation having an incident intensity at said subject and obtaining relative intensity signals representing relative intensity values for radiation passing through said subject;
   generating data representing an image of said examination subject, said image conforming to parallel slices of said examination subject, by spiral interpolation of said relative intensity values performed directly on said relative intensity signals; and
   constructing said image of said examination subject from said data.

4. A method as claimed in claim 3 wherein the step of generating data is further defined by spirally interpolating said relative intensity signals of a plurality of said parallel slices, each slice having a center and said centers having a center spacing therebetween, to obtain interpolated intensities by the steps of:
   multiplying a relative intensity for a first parallel slice by the sum of one plus the quotient of the center for said first parallel slice divided by said center spacing, and subtracting therefrom a relative intensity signal for a second parallel slice spaced from said first parallel slice by said center spacing and multiplied by the quotient of said center for said first parallel slice divided by said center spacing; and
   wherein the step of constructing said image is further defined by constructing said image with attenuation values obtained by a multiplication factor multiplied by the natural logarithm of the quotient of said relative intensities divided by said incident intensity.

* * * * *